(12) United States Patent
Einaga et al.

(10) Patent No.: US 9,625,405 B2
(45) Date of Patent: Apr. 18, 2017

(54) OZONE WATER CONCENTRATION MEASUREMENT APPARATUS AND OZONE WATER CONCENTRATION MEASUREMENT METHOD

(71) Applicants: KEIO UNIVERSITY, Minato-ku, Tokyo (JP); NIKKA MICRON CO., LTD., Misato-shi, Saitama (JP)

(72) Inventors: Yasuaki Einaga, Yokohama (JP); Ivandini Tribidasarianggraningrum, Yokohama (JP); Yuya Ishii, Yokohama (JE); Shigeo Sekiguchi, Misato (JP); Kazutaka Murata, Misato (JP)

(73) Assignees: KEIO UNIVERSITY, Tokyo (JP); NIKKA MICRON CO., LTD., Misato-Shi, Saitama (JP)

( * ) Notice: Subject to any disclaimer, the term of this patent is extended or adjusted under 35 U.S.C. 154(b) by 2 days.

(21) Appl. No.: 14/441,984

(22) PCT Filed: Aug. 27, 2013

(86) PCT No.: PCT/JP2013/072831
§ 371 (c)(1),
(2) Date: May 11, 2015

(87) PCT Pub. No.: WO2014/077017
PCT Pub. Date: May 22, 2014

(65) Prior Publication Data
US 2015/0330929 A1    Nov. 19, 2015

(30) Foreign Application Priority Data

Nov. 16, 2012 (JP) .................................. 2012-251851

(51) Int. Cl.
*C25D 17/00* (2006.01)
*G01N 27/26* (2006.01)
(Continued)

(52) U.S. Cl.
CPC ......... *G01N 27/07* (2013.01); *G01N 27/4168* (2013.01); *G01N 33/18* (2013.01)

(58) Field of Classification Search
CPC ..... G01N 27/07; G01N 33/18; G01N 27/4168
USPC .................................. 324/693; 204/266, 400
See application file for complete search history.

(56) References Cited

U.S. PATENT DOCUMENTS

| | | | | |
|---|---|---|---|---|
| 2002/0157946 A1* | 10/2002 | Winquist | ........... | G01N 33/0039 204/400 |
| 2010/0148780 A1* | 6/2010 | Lawrence | .......... | G01N 33/2841 324/324 |

FOREIGN PATENT DOCUMENTS

| | | |
|---|---|---|
| JP | 2003262612 A | 9/2003 |
| JP | 2007212232 A | 8/2007 |

(Continued)

OTHER PUBLICATIONS

International Preliminary Report on Patentability (IPRP) including Written Opinion (in English) dated May 19, 2015, issued in parent International Application No. PCT/JP2013/072831.

(Continued)

*Primary Examiner* — Farhana Hoque
(74) *Attorney, Agent, or Firm* — Holtz, Holtz & Volek PC

(57) ABSTRACT

An ozone water concentration measurement apparatus that is capable of measuring ozone concentrations with high accuracy and without using an electrolyte brings at least a counter electrode and a working electrode into contact with ozone water, which is a sample solution (S), applies voltage between the counter electrode and the working electrode, and measures the current value at that voltage, to thereby calculate the ozone concentration in the ozone water. In the ozone water concentration measurement apparatus, the working electrode is a conductive diamond electrode, and (Continued)

the surface area that contacts the ozone water of the working electrode is within the range of 628 to 392,500 µm².

6 Claims, 8 Drawing Sheets

(51) Int. Cl.
    *G01N 27/07*     (2006.01)
    *G01N 33/18*     (2006.01)
    *G01N 27/416*     (2006.01)

(56) References Cited

FOREIGN PATENT DOCUMENTS

| | | | |
|---|---|---|---|
| JP | 2007292717 A | 11/2007 | |
| JP | 2008281356 A | 11/2008 | |

OTHER PUBLICATIONS

Yasuaki Einaga, "Applications of Boron-doped Diamond Electrodes to Electrochemical Sensors", Surface Science, 2008, vol. 29, No. 3, pp. 164-172.

International Search Report (ISR) dated Oct. 8, 2013 issued in International Application No. PCT/JP2013/072831.

Japanese Office Action dated Dec. 25, 2012 issued in counterpart Japanese Application No. 2012-251851.

Taiwanese Office Action dated Dec. 5, 2014 issued in counterpart Taiwanese Application No. 102141023.

Y. Einaga, et al., "Diamond Diamond Like Carbon (DLC) no Denki Kagaku eno Tenkai 2, 1 Diamond Denki Kagaku no Tenkai", Electrochemistry, 2009, vol. 77, No. 4, pp. 341-349.

Chinese Office Action dated Apr. 1, 2016, issued in counterpart Chinese Application No. 201380059891.1.

"Application of boron-containing diamond film electrodes", Advanced Superabrasives and Related Products (2nd Volume), First Edition, Edited by Xiaohu Fang et al, Zhejiang University Press, Nov., 2011: p. 678.

Chinese Office Action (and English translation thereof) dated Nov. 22, 2016 issued in counterpart Chinese Application No. 201380059891.1.

"Micro-electrode", Analytical Chemistry 5th edition, 2nd Volume. Edited by Wuhan University, Higher Education Press, Dec., 2007: p. 460.

\* cited by examiner

OZONE WATER CONCENTRATION MEASUREMENT APPARATUS AND OZONE WATER CONCENTRATION MEASUREMENT METHOD

TECHNICAL FIELD

The present invention relates to an ozone water concentration measurement apparatus and an ozone water concentration measurement method using an electrochemical method.

BACKGROUND ART

Ozone water is known to be beneficial in many fields due to its sterilizing property, deodorizing property, effects on cells and the like. Furthermore, ozone does not affect the respiratory organs when it is dissolved in water. Accordingly, ozone water has been widely used in medical and nursing fields as well as industrial fields. However, due to the short time in which the concentration of ozone water decays, there is a strong demand for the concentration to be selected and checked on the site where ozone water is used.

One conventional ozone water concentration measurement method is iodine/pigment titration, which displays the change in color of a reagent such as potassium iodide. However, a problem with this method is that the measurement values differ between individual measurers due to the reliance on a visual determination by a measurer. Furthermore, this method requires liquid waste disposal following the measurement and there is a high cost for preparing the reagent. Furthermore, this operation is not easy, and such a complicated operation prevents the practical use thereof in typical sites where ozone water is used.

For these reasons, the method currently in use is an ultraviolet absorption method that determines the ultraviolet absorption rate of ozone water, or diaphragm-type polarography, in which electrodes and an electrolyte are shielded from ozone water, i.e. a sample solution, by a highly ozone-permeable diaphragm, and the ozone concentration is determined from the electric current when a constant voltage is applied between the electrodes, which increases proportionally to the amount of ozone that has penetrated the diaphragm and diffused in the electrolyte.

However, the problem with the ultraviolet absorption method is that it is very expensive and it is difficult to precisely measure the concentration due to ozone bubbles that scatter light transmitted from an ultraviolet absorption ozone water concentration meter. The diaphragm polarography uses a diaphragm and an electrolyte such as hydrogen peroxide, persulfic acid, a fluorine acid and a chlorine acid. Therefore, the diaphragm and the electrolyte require periodic maintenance. Further, some electrolytes may have a problem of liquid waste disposal and there is the danger that the electrolyte will corrode the electrodes.

To cope with these problems, a concentration measurement method known in the art does not use a diaphragm and also prevents the electrolyte from corroding the electrodes, in which the use of an electrically conductive diamond for a working electrode enables the working electrode to be directly dipped in ozone water, and the ozone concentration is measured from a change in the electric current value between the working electrode and a counter electrode when a changing voltage is applied between a reference electrode and the working electrode (e.g. see Patent Document 1). The working electrode described in Patent Document 1 is constituted by a silicon substrate with a thin film of boron-doped diamond formed thereon. The working electrode has a comparatively large size with an outer diameter of approximately 4 mm to 5 mm.

In a concentration measurement apparatus that uses a working electrode, a counter electrode and a reference electrode as described above, the voltage $E_{appl}$ between the working electrode and the reference electrode corresponds to the electrode potential to be regulated. When a current I flows between the working electrode and the counter electrode, the voltage falls by a value $IR_{sol}$ (where $R_{sol}$ is the effective resistance of a solution between the working electrode and a tip of the reference electrode). (This phenomenon is also referred to as IR drop.) That is, the voltage E actually applied to the electrode surface (sample solution) is decreased by the amount of voltage drop, which is represented by $E = E_{appl} - IR_{sol}$. When the sample solution is pure ozone water that contains no electrolyte and a large electrode is used that has an outer diameter of approximately 4 mm to 5 mm like the working electrode described in Patent Document 1, the large surface area of contact with the sample solution greatly increases the solution resistance $R_{sol}$ and the current I, and the resultant voltage drop becomes too large to ignore. As a result, the voltage E actually applied to the sample solution becomes much lower than the voltage $E_{appl}$ between the working electrode and the reference electrode. This decreases the electric current flowing between the working electrode and the counter electrode to a level that is too low to be precisely measured. Accordingly, it is impossible to precisely measure the ozone concentration from such a low electric current.

Therefore, in the case in Patent Document 1, the use of an electrolyte is essential in order to decrease the solution resistance $R_{sol}$. However, this causes problems with the electrolyte, such as liquid waste disposal and handling difficulties.

Prior Art Document

Patent Document

Patent Document 1: JP 2007-212232A

SUMMARY OF INVENTION

Problem to be Solved by the Invention

The present invention was made in view of the above circumstances, and an object thereof is to provide an ozone water concentration measurement apparatus and an ozone water concentration measurement method that can measure ozone concentration with high accuracy without using an electrolyte.

Means for Solving the Problem

In the course of a study to ascertain the cause of the above-described problems in order to solve them, the present inventors found that the voltage drop is decreased to a negligible level by using electrically conductive diamond as a working electrode and by decreasing rather than increasing the area of contact between the working electrode and the ozone water to be a very small surface area, such as within the range of 628 μm² to 392500 μm². Therefore, even when no electrolyte is used, and when the sample solution is high-resistance pure ozone water, the electric current can be precisely measured and the concentration of ozone water can be measured with high accuracy. The present invention was thus complete.

That is, the above problems related to the present invention are solved by the following means.

1. An ozone concentration measurement apparatus that calculates ozone concentration of ozone water by bringing at least a counter electrode and a working electrode into contact with a sample solution of the ozone water and by applying a voltage between the counter electrode and the working electrode to measure an electric current value at the voltage, wherein the working electrode is constituted by an electrically conductive diamond electrode, and wherein a surface area of contact between the working electrode and the ozone water is within a range of 628 $\mu m^2$ to 392500 $\mu m^2$.

2. The ozone water concentration measurement apparatus according to claim 1, wherein the electrically conductive diamond electrode is constituted by a boron-doped electrically conductive diamond electrode.

3. An ozone water concentration measurement method for measuring ozone concentration of ozone water, including the steps of:

bringing at least a counter electrode and a working electrode into contact with a sample solution of the ozone water;

applying a voltage between the counter electrode and the working electrode; and measuring an electric current value at the voltage, wherein the working electrode is constituted by an electrically conductive diamond electrode, and wherein a surface area of contact between the working electrode and the ozone water is within a range of 628 $\mu m^2$ to 392500 $\mu m^2$.

4. The ozone water concentration measurement method according to claim 3, wherein no electrolyte is contained in the sample solution.

5. The ozone water concentration measurement method according to claim 3 or 4, wherein the electrically conductive diamond electrode is constituted by a boron-doped electrically conductive diamond electrode.

Effects of Invention

With the present invention, ozone concentration can be measured with high accuracy without using an electrolyte.

The mechanism of how the present invention develops and produces the advantageous effects has not yet been revealed, but it is presumed as follows.

In the present invention, the working electrode is constituted by an electrically conductive diamond electrode, and the surface area of contact between the working electrode and the ozone water is within the range of 628 $\mu m^2$ to 392500 $\mu m^2$. Since such an extremely small electrode comes into contact with ozone water, the electric current I flowing between the working electrode and the counter electrode during the measurement is decreased to a very low level, and the voltage drop ($IR_{sol}$) is decreased accordingly to a negligible level even when the solution is ozone water that does not include an electrolyte and has high solution resistance $R_{sol}$. As a result, the voltage actually applied to the sample solution becomes substantially equal to the originally applied voltage, which allows precise measurement of the electric current flowing between the working electrode and the counter electrode at the applied voltage. By using the measured electric current value, the concentration of the ozone water can be measured with high accuracy.

DESCRIPTION OF EMBODIMENTS

Primarily, the ozone water concentration measurement apparatus of the present invention calculates the ozone concentration of ozone water, i.e. a sample solution, by bringing at least a counter electrode and a working electrode into contact with the ozone water and by applying a voltage between the counter electrode and the working electrode to measure an electric current value at the voltage. The working electrode is constituted by an electrically conductive diamond electrode, and the surface area of contact between the working electrode and the ozone water is within the range of 628 $\mu m^2$ to 392500 $\mu m^2$.

In an embodiment of the present invention, it is preferred that the electrically conductive diamond electrode is constituted by a boron-doped electrically conductive diamond electrode in terms of obtaining the advantageous effects of the present invention.

Primarily, the ozone water concentration measurement method according to the present invention involves calculating the ozone concentration of ozone water, i.e. a sample solution, by bringing at least a counter electrode and a working electrode into contact with the ozone water and by applying a voltage between the counter electrode and the working electrode to measure an electric current value at the voltage. The working electrode is constituted by an electrically conductive diamond electrode, and the surface area of contact between the working electrode and the ozone water is within the range of 628 $\mu m^2$ to 392500 $\mu m^2$.

It is preferred that no electrolyte is added to the sample solution in order to negate the problem of electrolyte liquid waste disposal and to facilitate handling the sample solution.

Hereinafter, the present invention and the components thereof, and designs and embodiments for carrying out the present invention will be described in detail. As used herein, the symbol "-" is used to mean that the values before and after it are included in the range as its lower limit and upper limit.

Ozone Water Concentration Measurement Apparatus

Figure 1:
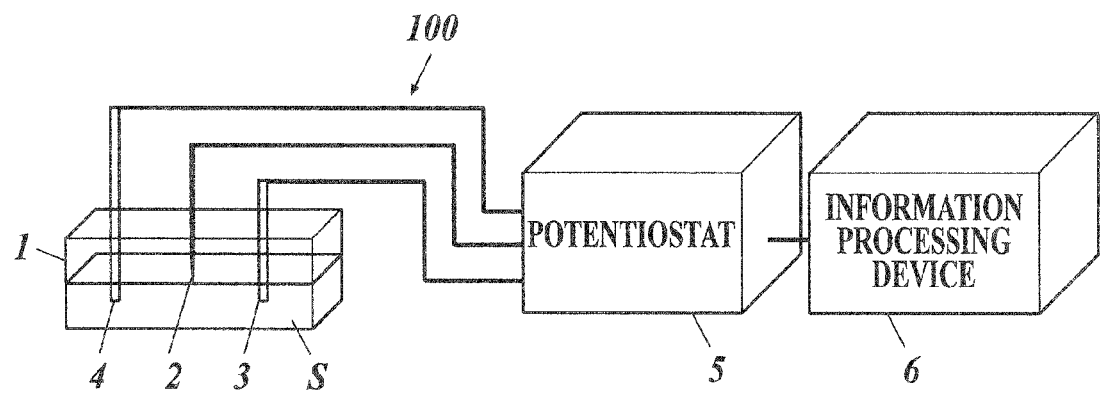
FIG. 1 This is a schematic view of the outline of an ozone water concentration measurement apparatus according to the present embodiment.

FIG. 1 is a schematic view of the outline of the ozone water concentration measurement apparatus of the present invention.

An ozone water concentration measurement apparatus 100 is a batch-type electrochemical measurement apparatus that applies a voltage to a sample solution S to perform three-electrode voltammetric measurement for analyzing the sample solution S.

In the present invention, the sample solution S is composed of only ozone water that contains no electrolyte and has high solution resistance.

The ozone water concentration measurement apparatus 100 includes: a measurement cell 1 in which the ozone water, i.e. the sample solution S, is stored; a working electrode 2 provided to be capable of contacting with the sample solution S in the measurement cell 1; a reference electrode 3 and a counter electrode 4; a potentiostat 5 that controls the voltage at the working electrode 2, the reference electrode 3 and the counter electrode 4; and an information processing device 6 that calculates the ozone concentration of the ozone water based on an electric current value and a voltage value obtained from the potentiostat 5.

Working Electrode

The working electrode 2 is configured to apply a voltage to the ozone water, which is the sample solution S. The working electrode 2 is formed in a stick shape with an approximately round cross-section or a thin plate shape with an approximately round cross-section.

The working electrode 2 is constituted by an electrically conductive diamond microelectrode and the surface area of contact with the sample solution S is within the range of 628 µm$^2$ to 392500 µm$^2$.

To make the surface area of contact between the working electrode 2 and the sample solution S fall within the above-described range, for example, only the tip of the working electrode 2 that has a tip outer diameter within the range of 20 µm to 500 µm (the hemispherical portion of the tip of the working electrode 2) may be brought into contact with the water surface of the sample solution S. That is, it is preferred that the surface area of contact with the sample solution S corresponds to the surface area of the hemispheric portion of the tip of the working electrode 2.

Specifically, when the outer diameter of the tip of the working electrode 2 is 20 µm, the surface area of contact with the sample solution S (the surface area of the hemispherical portion of the tip of the working electrode 2) is 10 µm×10 µm×2×3.14=628 µm$^2$.

When the outer diameter of the tip of the working electrode 2 is 500 µm, the surface area of contact with the sample solution S is 250 µm×250 µm×2×3.14=392500 µm$^2$.

The only requirement is that the surface area of contact with the sample solution S is within the above-described range. Instead of bringing only the tip of the working electrode 2 into contact with the water surface of the sample solution S, a portion within a suitable length from the tip of the working electrode 2 may be brought into contact with the sample solution S as long as the surface area is within the above-described range.

FIG. 1 illustrates an example of a stick electrode with an approximately round cross-section.

The surface area of contact between the working electrode 2 and the sample solution S is within the range of 628 µm$^2$ to 392500 µm$^2$ because it is difficult to produce the working electrode 2 when the surface area is less than 628 µm$^2$.

When the surface area is greater than 392500 µm$^2$, the solution resistance causes the IR drop to become too large to ignore in the absence of an electrolyte. Accordingly, the voltage E actually applied to the sample solution S becomes much lower than the applied voltage $E_{appl}$ between the working electrode 2 and the reference electrode 3, and the electric current value between the working electrode 2 and the counter electrode 4 becomes too low to measure precisely. It is difficult to calculate the ozone concentration from such a low electric current value.

The electrically conductive diamond electrode is preferably constituted by, for example, a boron-doped electrically conductive diamond electrode. Instead of boron, an electrode of an electrically conductive diamond doped with a Group 13 or Group 15 element such as nitrogen and phosphorous may also be used.

The use of such electrically conductive diamond electrodes provides advantageous effects such as wide potential window (wide range of the oxidation potential and the reduction potential) and low background current compared to other electrode materials. In particular, a boron-doped electrically conductive diamond electrode has high chemical resistance, good durability, high electrical conductivity and high resistance to corrosion and the like.

When boron is doped, the amount of boron dope is preferably within the range of 0.1% to 8%, more preferably within the range of 0.1% to 1% with respect to diamond (carbon). The amount of dope is limited within the range of 0.1% to 8% for the following reasons. When the amount is less than 0.1%, the electrode becomes almost an insulating material due to the decreased electrical conductivity, and it cannot work as an electrode. When the amount is greater than 8%, it is theoretically difficult to produce such diamond, and such high-concentration boron dope disrupts the diamond structure.

Next, a method for producing the electrically conductive diamond microelectrode according to the present invention will be described.

An electrically conductive diamond stick electrode with an approximately round cross-section can be produced by forming an impurity-doped (e.g. boron-doped) diamond film on a stick substrate with an approximately round cross-section by means of microwave plasma CVD.

A specific production method is as follows.

For a stick substrate, for example, a tungsten wire, a platinum wire, a molybdenum wire or the like is used. The substrate is machined beforehand such that at least the outer diameter of the tip is smaller than a value within the range of 20 µm to 500 µm by the film thickness of the diamond (e.g. 1 µm to 5 µm). The length of the substrate is preferably within the range of 10 mm to 25 mm.

For a carbon source, aceton, methane gas, ethanol, methanol and the like can be used. For a boron source, trimethoxyborane, trimethylboron, boron oxide and the like can be used. In particular, liquid trimethoxyborane is preferably used for the boron source for safety reasons and for easy handling. When acetone is used as the carbon source and trimethoxyborane is used as the boron source, a liquid mixture of acetone and trimethoxybonane in predetermined ratio is vaporized by bubbling carrier gas of hydrogen to prepare a material gas, which is then introduced into a chamber.

Figure 2:
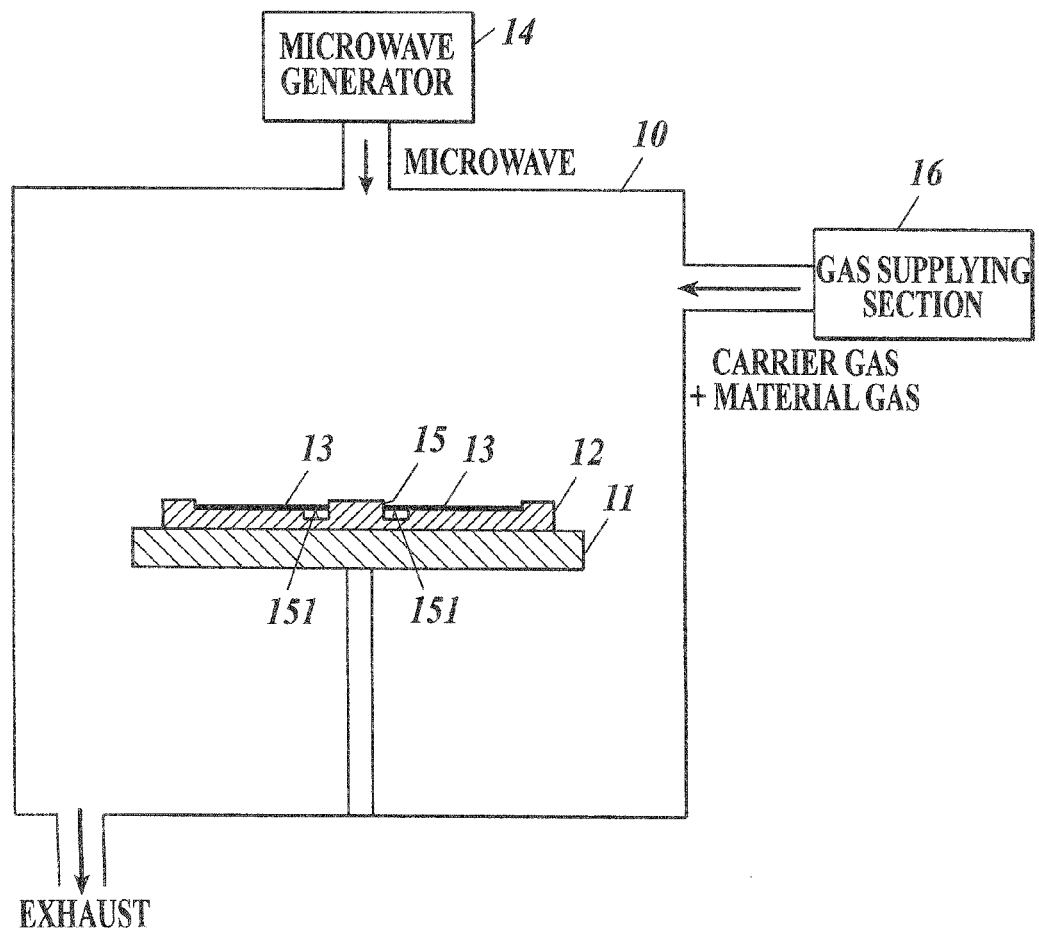
FIG. 2 This is a schematic view of the outline of a microwave plasma CVD apparatus.
Figure 3:
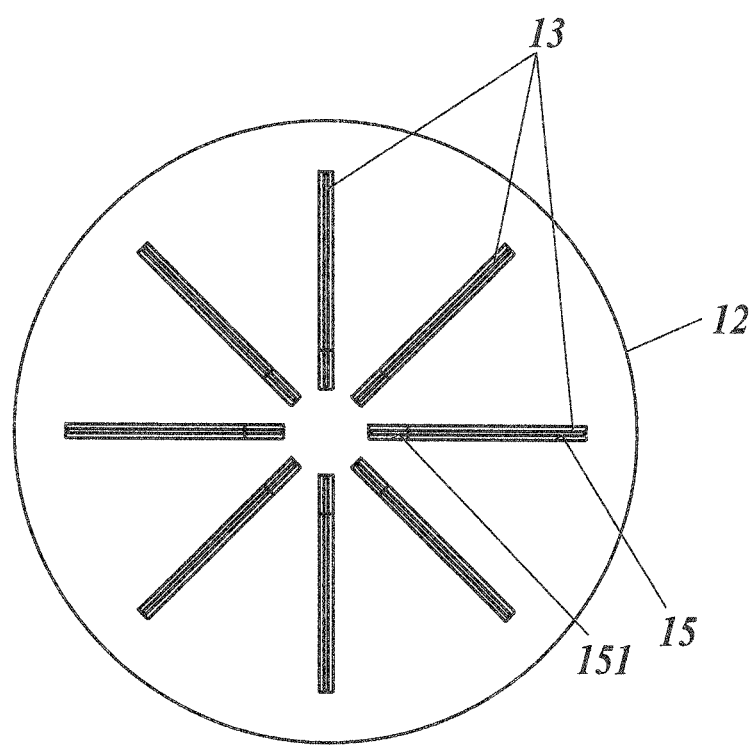
FIG. 3 This is a plan view of a substrate and a holder of FIG. 2.

As illustrated in FIG. 2, first, a plurality of substrates 13 are radially mounted on a holder 12 disposed on a stage 11 in a chamber 10. The holder 12 has a plurality of grooves 15 for mounting the substrates 13, and the substrates 13 are individually placed in the grooves 15.

Each groove 15 has a downward recess 151 at a location corresponding to the tip of each substrate 13. The recesses 151 allow the material gas to reach the lower faces of the substrates 13 so that uniform films can be formed on the substrates 13.

Then, hydrogen gas for generating plasma is introduced into the chamber 10 through a different line from a gas supplying section 16 (not shown), and plasma is generated beforehand by means of a microwave generator 14. Subsequently, the material gas (trimethoxyborane+acetone) vaporized by the carrier gas is introduced into the chamber 10 through the gas supplying section 16. Then, the material gas introduced into the chamber 10 is changed to plasma and forms a diamond film on the whole surface of the substrates 13.

The electrically conductive diamond microelectrode thus formed is in the as-grown condition (the crystal is not subjected to any treatment such as surface treatment after it is grown on the substrate), and the surface is mostly hydrogen-terminated. In order to make a fully hydrogen-terminated surface of the electrically conductive diamond, it is preferred that the as-grown electrically conductive diamond electrode is subjected to cathodic reduction by immersing it in 0.1 M sulfuric acid ($H_2SO_4$) for 30 minutes while applying a voltage of −1.8 V.

The method for hydrogen termination of the surface of the electrically conductive diamond is not limited to the above-described cathodic reduction, but may be other methods such as heating at 700° C. or more under hydrogen atmosphere.

Instead of the hydrogen termination, the surface of the electrically conductive diamond electrode may be oxygen-terminated. In the present invention, the oxygen-terminated surface is preferred in terms of achieving high sensitivity. A method for oxygen termination is anodic oxidation that involves immersing the above-described as-grown electrically conductive diamond electrode in 0.1 M perchloric acid for 30 min while applying a voltage of 3.0 V. The oxygen termination may be performed by other methods such as an oxygen plasma treatment.

The working electrode 2 thus produced is fixed by means of a holding member (not shown) such that the surface area of contact with the ozone water stored in the measurement cell 1 is within the above-described range.

An electrically conductive diamond thin plate electrode with an approximately round cross-section can be produced, for example, by the following method.

Figure 4A:
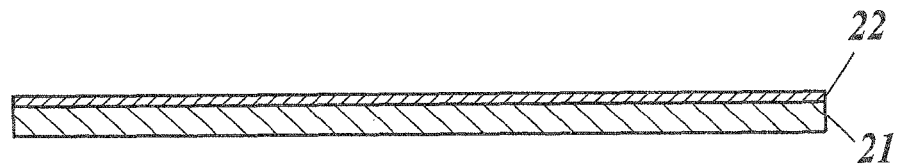
FIG. 4A This is a cross sectional view illustrating an example of a method for producing a conductive diamond electrode.

First, as illustrated in FIG. 4A, a film of an impurity-doped (e.g. boron-doped) diamond 22 is formed on a flat plate substrate 21 with a diameter of 50 mm (φ50) and a thickness of 0.8 mm (t=0.8) by means of the above-described microwave plasma CVD. For the flat plate substrate 21, for example, a silicon wafer can be used.

Figure 4B:
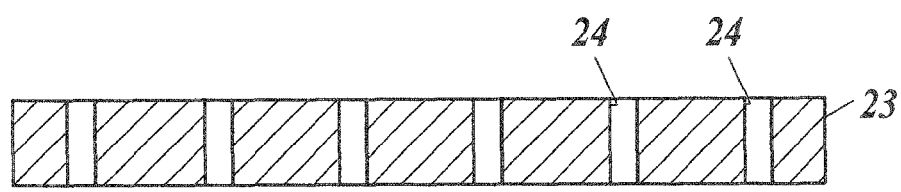
FIG. 4B This is a cross sectional view illustrating the step following FIG. 4A.

Thereafter, as illustrated in FIG. 4B, a plurality of holes 24 with an outer diameter within the range of 30 μm to 700 μm are formed in a flat plate insulating substrate 23 with a diameter of 50 mm (50) and a thickness of 1.5 mm (t=1.5) by means of a laser or the like. For the insulating substrate 23, for example, a glass substrate can be used.

Figure 4C:
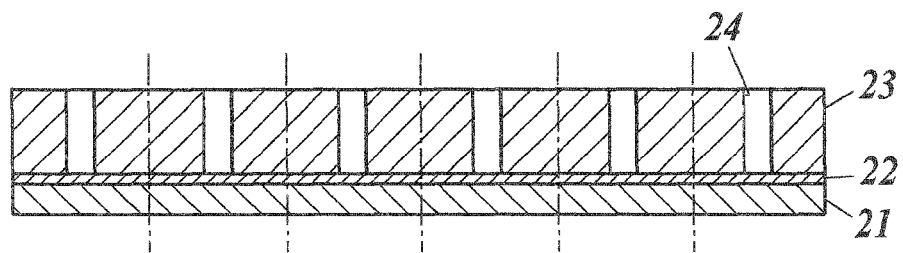
FIG. 4C This is a cross sectional view illustrating the step following FIG. 4B.

Then, as illustrated in FIG. 4C, the substrate 21 with the film formed thereon and the insulating substrate with the holes 24 formed therein are joined to each other by means of anodic bonding.

Figure 4D:
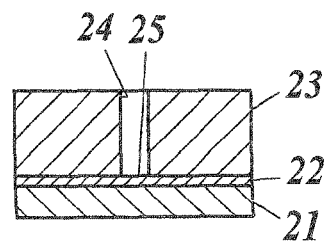
FIG. 4D This is a cross sectional view illustrating the step following FIG. 4C.

Lastly, as illustrated in FIG. 4D, the joined substrates 21 and 23 are diced and singulated into, for example, square chips of 1.5 mm×1.5 mm. Then, an individual singulated chip is disposed such that the electrically conductive diamond film portion 25 exposed in a hole 24 comes into contact with the ozone water, and is thus used as the working electrode. In this way, the surface area of contact between the electrically conductive diamond film portion 25 and the ozone water falls within the range of the present invention.

Reference Electrode

The reference electrode 3 serves as a reference for the potential of the working electrode 2.

For the reference electrode 3, for example, a silver/silver chloride electrode (Ag/AgCl electrode), a standard hydrogen electrode, a mercury/mercury chloride electrode, a hydrogen palladium electrode and the like can be used.

The reference electrode 3 is fixed by means of a holding member (not shown) such that it comes into contact with the ozone water stored in the measurement cell 1.

Counter Electrode

The counter electrode 4 allows an electric current to flow through the working electrode 2 unhindered when the working electrode 2 is set at a certain potential and is connected to the working electrode 2 in series.

For the counter electrode 4, for example, platinum (Pt), carbon, stainless steel, gold, diamond, $SnO_2$ and the like can be used.

As with the reference electrode 2, the counter electrode 4 is also fixed by a holding member (not shown) such that it comes into contact with the ozone water stored in the measurement cell 1.

The distance between the working electrode 2, the reference electrode 3 and the counter electrode 4 is preferably within the range of 5 mm to 20 mm. In terms of further decreasing the voltage drop, the distance between the electrodes is preferably 10 mm.

Potentiostat

The potentiostat 5 exerts a function as a voltage applying section to apply a voltage to the working electrode 2, the reference electrode 3 and the counter electrode 4, and a function as an electric current measuring section to measure the electric current value at the applied voltage.

The potentiostat 5 is controlled by the information processing device 6 so as to receive voltage signals and electric current signals from the working electrode 2, the reference electrode 3 and the counter electrode 4 and also to control the working electrode 2, the reference electrode 3 and the counter electrode 4.

That is, the potentiostat 5 sweeps the voltage applied to the working electrode 2, which corresponds to the potential with respect to the reference electrode 3, within a predetermined range, and measures the response electric current flowing between the working electrode 2 and the counter electrode 4 during the potential sweep.

Specifically, the potentiostat 5 scans the potential of the working electrode 2 with respect to the reference electrode 3, for example, between 1.0 V to −0.8 V at a rate of 100 mV/s, and measures the electric current value flowing between the working electrode 2 and the counter electrode 4 caused by a reduction reaction in the voltage.

Information Processing Device

The information processing device 6 determines a limiting current-voltage curve from the voltage swept within the predetermined range by the potentiostat 5 and from the response current values. Then, the ozone concentration is calculated from a limiting current value at a predetermined voltage (e.g. −0.2 V) on the limiting current-voltage curve based on a previously determined calibration curve.

The calibration curve is obtained by sweeping voltage within a predetermined range for ozone waters with known concentrations, measuring the response current flowing between the working electrode 2 and the counter electrode 4 during the sweep, determining limiting current-voltage curves from the voltage swept within the predetermined range and the response electric current values, and plotting the limiting current values at a predetermined voltage (e.g. −0.2 V) on the limiting current-voltage curves against the ozone concentrations.

The predetermined standard voltage on the limiting current-voltage curves for determining the calibration curve is not limited to the above −0.2 V but may be at any level where the limiting current values for respective known concentrations can be clearly determined.

On the other hand, when measuring the ozone concentration, the information processing device 6 controls the potentiostat 5 to change the potential of the working electrode 2 with respect to the reference electrode 3, for example, between 1.0 V to −0.8 V at a rate of 100 mV/s.

Specifically, the information processing device 6 includes a CPU, an internal memory, an external storage such as an HDD, a communication interface such as a modem, a display, and an input means such as a mouse and a keyboard.

The information processing device 6 analyzes electrical signals to calculate the ozone concentration according to a program set in a predetermined area such as the internal memory and the external storage. The information processing device 6 may be either a general-purpose computer or a dedicated computer.

The ozone water concentration measurement apparatus 100 according to the above-described embodiment performs the measurement based on a three-electrode method using the counter electrode 4, the working electrode 2 and the reference electrode 3. However, the present invention is not limited thereto, and the measurement may be based on a two-electrode method using only the counter electrode 4 and the working electrode 2. The measurement based on the three-electrode method has higher accuracy and higher sensitivity since the absolute value of the voltage applied between the working electrode 2 and the counter electrode 4 is controllable.

In contrast, the two-electrode method is preferred in that the flow cell can be simplified and reduced in size, and the measurement cell can be constituted by a disposable chip since only the two electrodes (namely, the counter electrode and the working electrode) are used.

Figure 5:
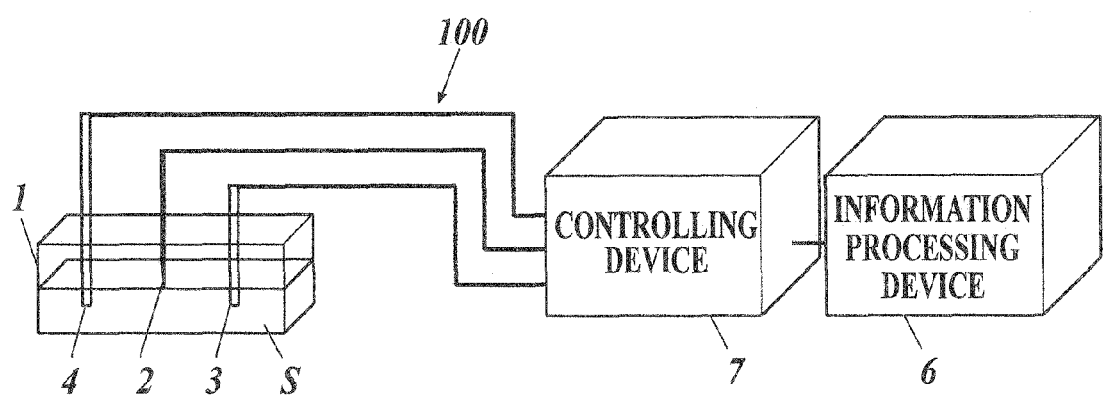
FIG. 5 This is a schematic view of the outline of an ozone water concentration measurement apparatus according to another embodiment.

The ozone water concentration measurement apparatus 100 according to the above-described embodiment is an example in which the potentiostat 5 sweeps the voltage applied to the working electrode 2, which corresponds to the potential with respect to the reference electrode 3, within a predetermined range. However, instead of using the potentiostat 5, as illustrated in FIG. 5, a controlling device 7 may be used. The controlling device 7 sweeps the voltage applied to the working electrode 2, which corresponds to the potential with respect to the reference electrode 3, with a constant voltage (e.g. 0.2 V) and measures the electric current flowing between the working electrode 2 and the counter electrode 4 at the voltage.

Next, the method for measuring ozone water concentration by using the ozone water concentration measurement apparatus 100 will be described.

Ozone Water Concentration Measurement Method

First, only a predetermined amount of ozone water is charged into the measurement cell 1 as the sample solution S.

Then, the working electrode 2 of the present invention is fixed by means of the holding member such that it is in contact with the water surface of the sample solution S. The surface area of contact between the working electrode 2 and the sample solution S is adjusted to fall within the above-described range. Further, the reference electrode 3 and the counter electrode 4 are fixed by means of the holding members such that they are in contact with the sample solution S and are arranged at a predetermined distance from each other.

Then, the potentiostat 5 sweeps the voltage applied to the working electrode 2, which corresponds to the potential with respect to the reference electrode 3, within the predetermined range and measures the response current flowing between the working electrode 2 and the counter electrode 4 during the potential sweep.

The information processing device 6 determines a limiting current-voltage curve from the voltage and the electric current values respectively swept and measured by the potentiostat 5, and calculates the ozone concentration from a limiting current value at a predetermined voltage (e.g. −0.2 V) on the limiting current-voltage curve based on the previously determined calibration curve.

As described above, in the embodiment of the present invention, the working electrode is constituted by an electrically conductive diamond electrode, and the surface area of contact between the working electrode and the ozone water is the range of 628 μm$^2$ to 392500 μm$^2$, i.e. an extremely small electrode is brought into contact with the ozone water. Accordingly, the current I flowing between the working electrode and the counter electrode is very low during the measurement, and the voltage drop ($IR_{sol}$) is negligibly small even when the ozone water contains no electrolyte additive and has high solution resistance $R_{sol}$. Accordingly, the voltage E actually applied to the sample solution is approximately equal to the voltage $E_{appl}$ applied between the working electrode and the reference electrode, and the electric current value flowing between the working electrode and the counter electrode can be precisely measured from the voltage $E_{appl}$. The ozone water concentration can be thus measured with high accuracy.

EXAMPLES

Next, advantageous effects of the ozone water concentration measurement apparatus of the present invention will be described with examples.

First, working electrodes of the following Example 1, Example 2, Example 3 and Comparison 1 were prepared.

Example 1

By using a microwave CVD apparatus (Comes Technologies Limited), an electrically conductive diamond electrode with an outer diameter of the tip of 20 μm was prepared by means of the microwave plasma CVD described below.

Specifically, a plurality of tungsten wires with a tip with an outer diameter of 15 μm and a length of 23 mm were used as stick substrates. They were radially mounted on a holder in a chamber of the microwave CVD apparatus. Then, hydrogen gas for generating plasma was introduced into the chamber to generate plasma. Then, acetone was used as a carbon source, trimethoxyborane was used as a boron source, and hydrogen gas was used as a carrier gas. A liquid mixture of acetone and trimethoxyborane in a predetermined ratio (the amount of boron dope is 1%) was vaporized by bubbling hydrogen gas, which was the carrier gas, so that a material gas was obtained. Then, the obtained material gas was introduced into the chamber through a different line from that of the hydrogen gas for plasma.

The introduction flow rate of the hydrogen gas for generating plasma into the chamber was set to 300 sccm. The flow rate of the material gas into the chamber was set to 10.8 sccm. The plasma power output was set to 2500 W. The inner pressure of the chamber was set to 60 Torr. The pressure of the carbon source was set to 18 to 22 Pa. The film forming time was set to 12 h. An electrically conductive diamond film with a film thickness of 2.5 μm was formed in these conditions.

As used herein, carbon source pressure refers to the pressure of the vaporized material gas (the carbon source (boron source) obtained by vaporizing acetone and trimethoxyborane through bubbling of the carrier gas) before being controlled by a valve to be introduced into the chamber. That is, it refers to the pressure of the vaporized carbon source (boron source) before passing through the valve.

The electrically conductive diamond electrode with a tip with an outer diameter of 20 μm thus prepared was used as the working electrode.

Figure 6:
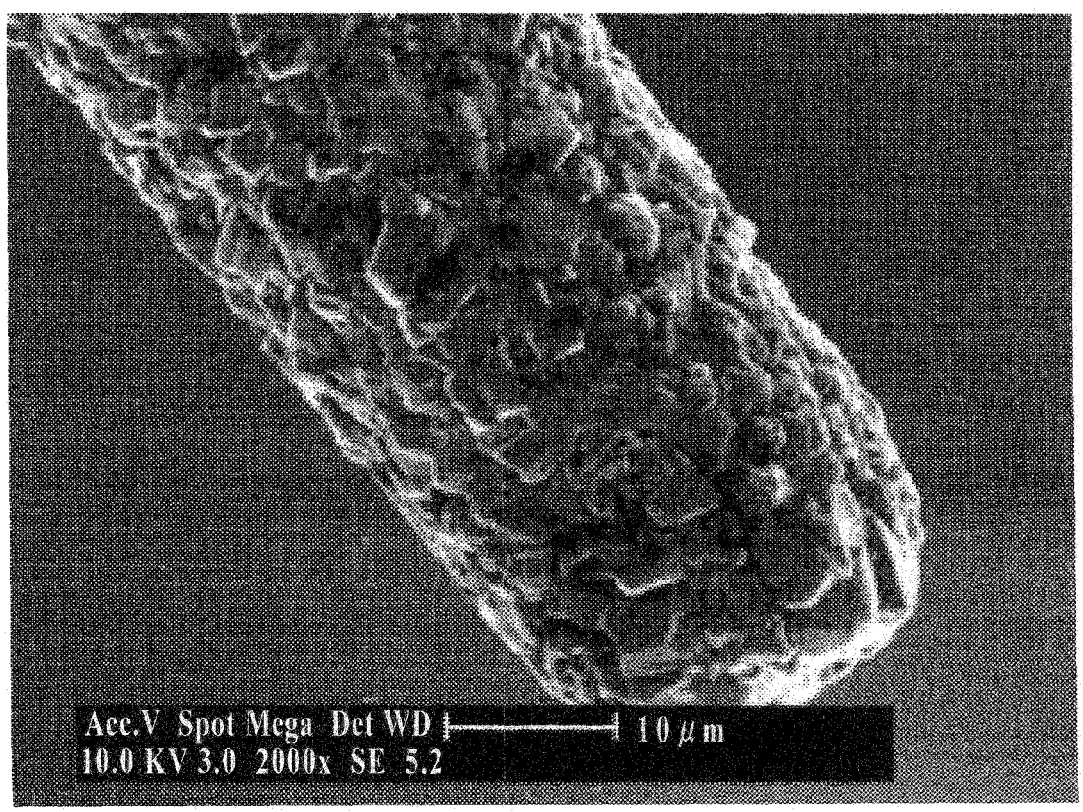
FIG. 6 This is a SEM photograph of an electrically conductive diamond electrode of Example 1.

FIG. 6 is a SEM photograph of the electrically conductive diamond electrode with a tip with an outer diameter of 20 μm prepared as described above.

Then, an ozone water concentration measurement apparatus equipped with the prepared working electrode, a silver/silver chloride electrode as a reference electrode and a platinum electrode as a counter electrode was prepared.

Ozone waters with four different concentrations were prepared as sample solutions, which were separately produced by using an ozone water generating apparatus. Then, 20 ml of the individual ozone waters were charged into different measurement cells. Then, the working electrode was disposed such that its tip was in contact with the water surface of the ozone water in a measurement cell. That is, the working electrode was disposed such that the surface area of contact with the ozone water was 628 μm$^2$ (10 m×10 μm×2×3.14).

The working electrode, the counter electrode and the reference electrode were disposed such that each distance between the electrodes was 10 mm.

The concentration of the ozone water, i.e. the sample solution, was measured using a known ozone meter. At the same time, limiting current values were measured by the ozone water concentration measurement apparatus prepared as described above while linearly sweeping the potential of the working electrode with respect to the reference electrode (100 mV/s). The obtained limiting current-voltage curve (voltammograms) is shown in FIG. 7.

Thereafter, limiting current was measured in the same manner for the ozone waters in the other measurement cells. The obtained limiting current-voltage curves are also shown in FIG. 7.

Figure 7:
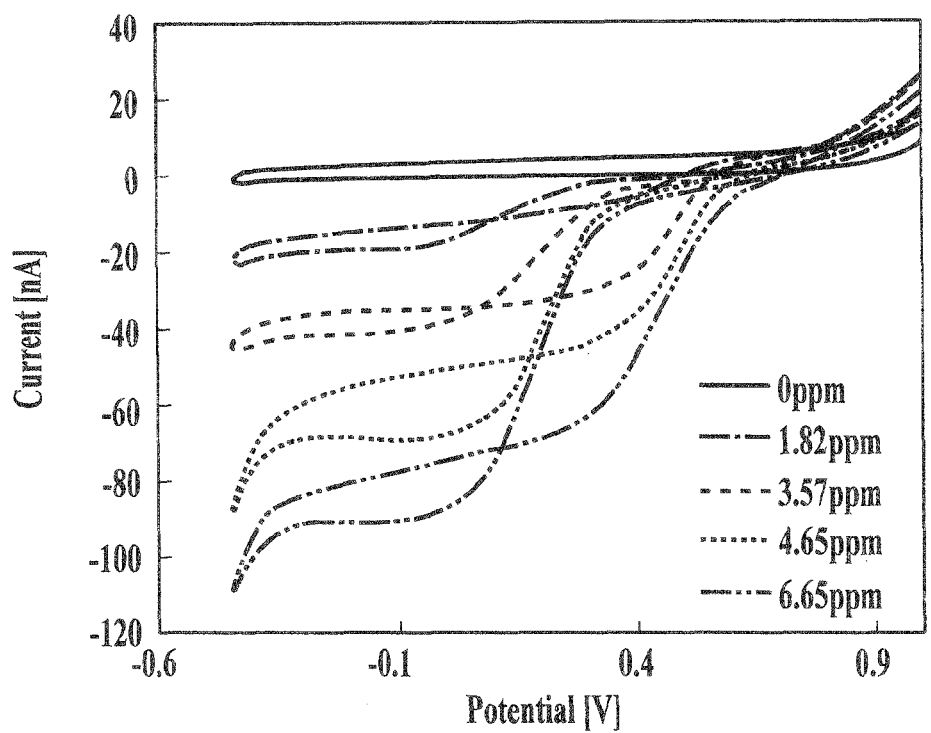
FIG. 7 This is a view of a limiting current-voltage curve (voltammogram) of Example 1.
Figure 11:
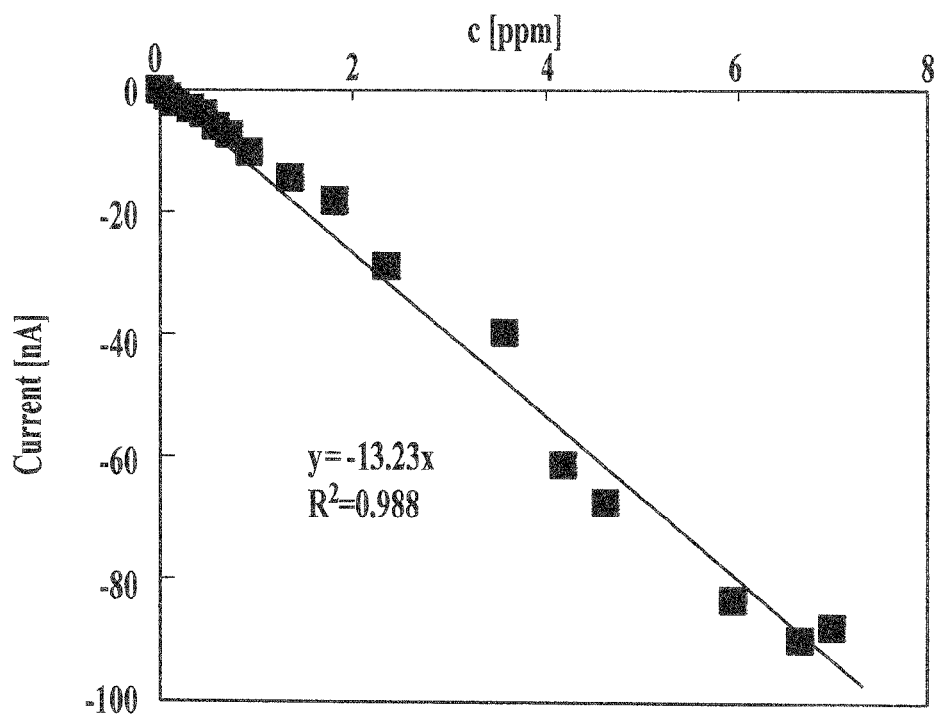
FIG. 11 This is a view of a calibration curve of ozone water concentration versus limiting current taken at –0.2 V of FIG. 7.

Based on the results shown in FIG. 7, the limiting current values at −0.2 V were plotted against the ozone concentrations measured by the known ozone mater such that the calibration curve shown in FIG. 11 was determined.

Example 2

The hydrogen-terminated electrically conductive diamond electrode obtained in Example 1 was anodized in 0.1 M perchloric acid at 3.5 V for 20 minutes so that an oxygen-terminated electrically conductive diamond electrode was prepared.

This electrically conductive diamond electrode was used as the working electrode.

Ozone waters with four different concentrations were prepared as sample solutions, which were separately produced using an ozone water generating apparatus. Then, 20 ml of the individual ozone waters were charged into different measurement cells. Then, the working electrode was disposed such that its tip was in contact with the water surface of the ozone water in a measurement cell. That is, the working electrode was disposed such that the surface area of contact with the ozone water was 628 μm$^2$.

The reference electrode, the counter electrode and the method of measuring limiting current value were the same as Example 1. The obtained limiting current-voltage curve (voltammogram) is shown in FIG. 8.

Thereafter, the limiting current of the ozone waters in other measurement cells was measured in the same manner. The obtained limiting current-voltage curves are also shown in FIG. 8.

Figure 8:
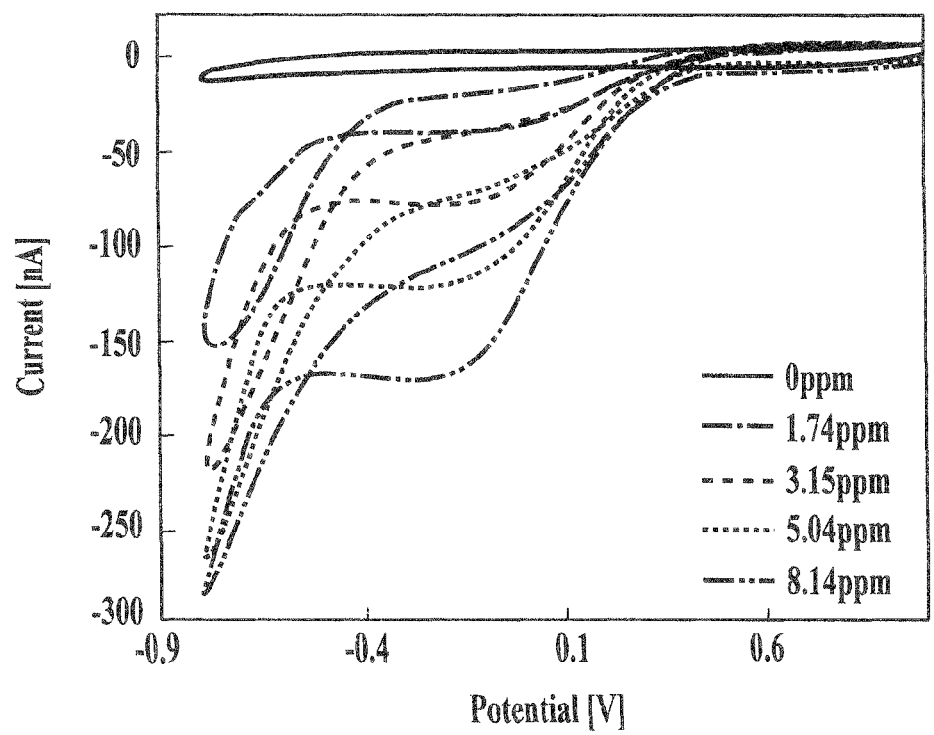
FIG. 8 This is a view of a limiting current-voltage curve (voltammogram) of Example 2.
Figure 12:
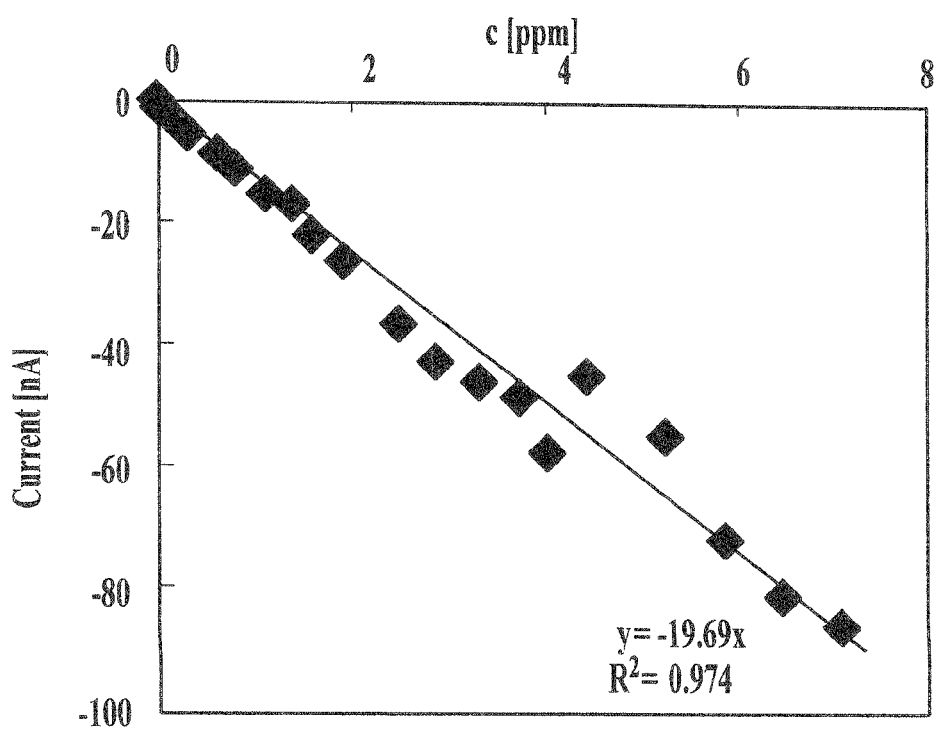
FIG. 12 This is a view of a calibration curve of ozone water concentration versus limiting current taken at –0.2 V of FIG. 8.

Based on the results shown in FIG. 8, the limiting current values at −0.2 V were plotted against the ozone concentrations measured by the known ozone meter so that the calibration curve shown in FIG. 12 was determined.

Example 3

An electrically conductive diamond film with a film thickness of 2.5 μm was formed in the same manner as Example 1 except that a tungsten wire with a tip with an outer diameter of 495 μm was used instead of the tungsten wire with a tip with an outer diameter of 15 μm and a length of 23 mm, so that a hydrogen-terminated electrically conductive diamond electrode with a tip with an outer diameter of 500 μm was prepared.

The obtained hydrogen-terminated electrically conductive diamond electrode was anodized in 0.1 M perchloric acid at 3.5 V for 20 min so that an oxygen-terminated electrically conductive diamond electrode was prepared.

This electrically conductive diamond electrode was used as the working electrode.

Ozone waters with four different concentrations were prepared as sample solutions, which were separately produced using an ozone water generating apparatus. Then, 20 ml of the individual ozone waters were charged into different measurement cells. Then, the working electrode was disposed such that its tip was in contact with the water surface of the ozone water in a measurement cell. That is, the working electrode was disposed such that the surface area of contact with the ozone water was 392500 μm$^2$ (=250 μm×250 μm×2×3.14).

The reference electrode, the counter electrode and the method of measuring limiting current value were the same as Example 1. The obtained limiting current-voltage curve (voltammogram) is shown in FIG. 9.

Thereafter, the limiting current of the ozone waters in the other measurement cells was measured in the same manner. The obtained limiting current-voltage curves are also shown in FIG. 9.

Figure 9:
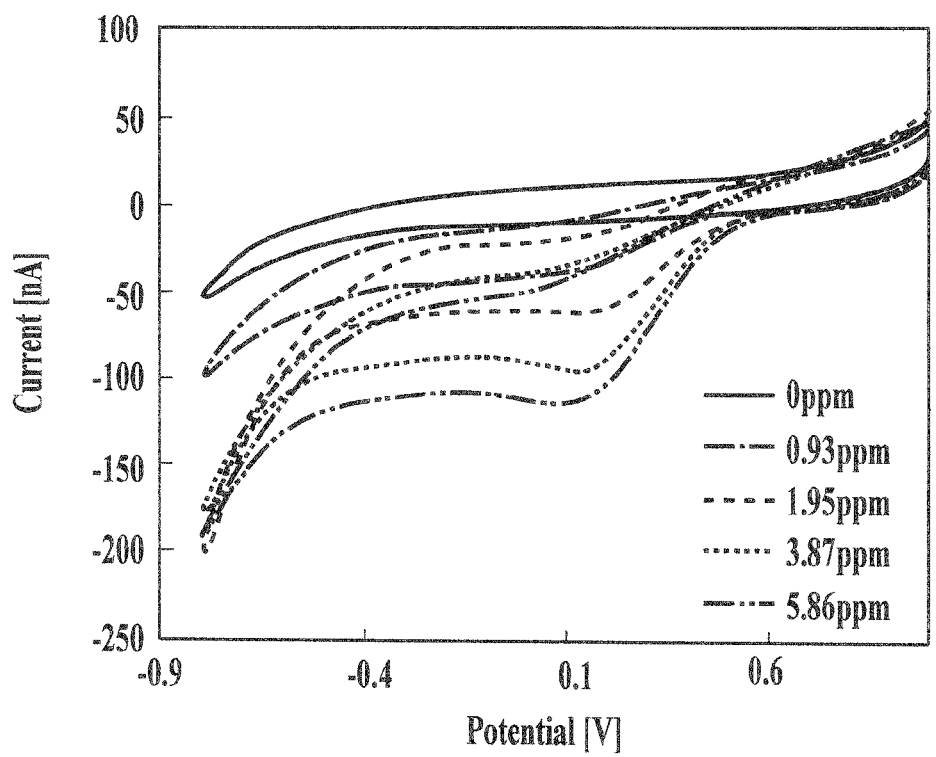
FIG. 9 This is a view of a limiting current-voltage curve (voltammogram) of Example 3.
Figure 13:
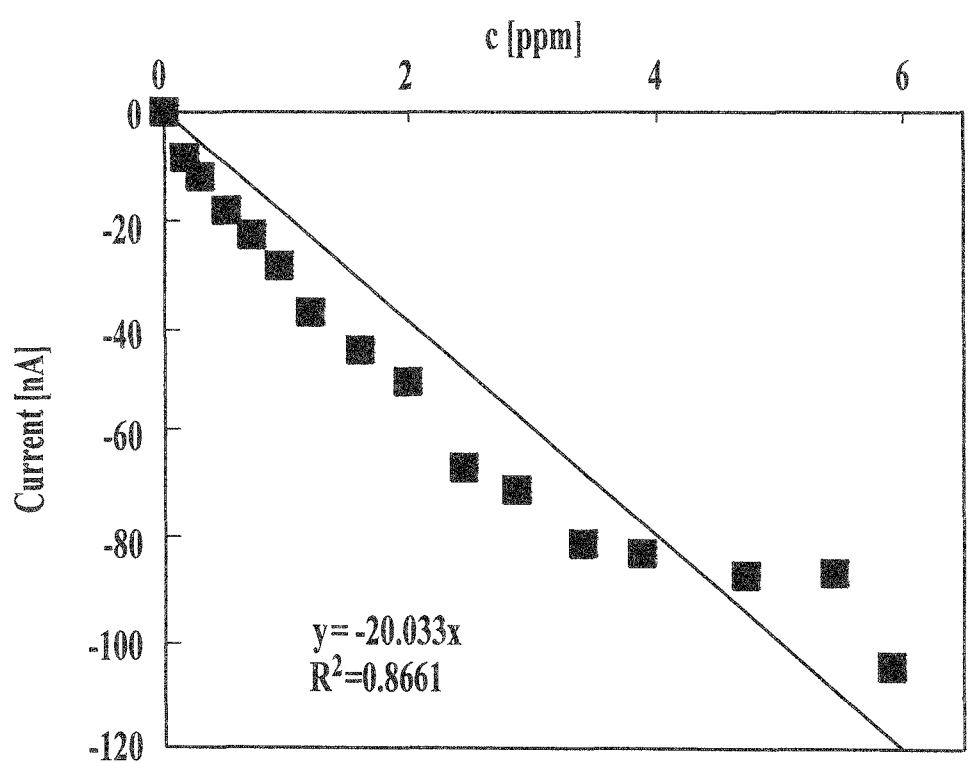
FIG. 13 This is a view of a calibration curve of ozone water concentration versus limiting current taken at –0.2 V of FIG. 9.

Based on the results shown in FIG. 9, the limiting current values at −0.2 V were plotted against the ozone concentrations measured by the known ozone meter so that the calibration curve shown in FIG. 13 was determined.

Comparison 1

A single-crystal silicon flat plate substrate is mounted on a holder in a chamber of a microwave CVD apparatus. Then, hydrogen gas for generating plasma was introduced into the chamber to generate plasma. Then, acetone was used as a carbon source, trimethoxyborane was used as a boron source, and hydrogen gas was used as a carrier gas. A liquid mixture of acetone and trimethoxyborane in a predetermined ratio (the amount of boron dope was 1%) was vaporized by bubbling hydrogen gas, which is the carrier gas, so that a material gas was obtained. Then, the material gas was introduced into the chamber through a different line from that of the hydrogen gas for plasma.

The introduction flow rate of the hydrogen gas for generating plasma into the chamber was set to 532 sccm. The flow rate of the material gas into the chamber was set to 10.8 sccm. The plasma power output was set to 5000 W. The inner pressure of the chamber was set to 120 Torr. The pressure of the carbon source was set to 2800 Pa. The film forming time was set to 8 h. An electrically conductive diamond film with a film thickness of 10 μm was formed in these conditions.

A 2 mm-diameter O-ring was placed on the silicon substrate with the diamond film formed thereon, and a cell was further disposed thereon. The area inside the cell was used as a hydrogen-terminated electrically conductive diamond electrode with an outer diameter of 2 mm.

Ozone waters with four different concentrations were prepared as sample solutions, which were separately produced using an ozone water generating apparatus. Then, 20 ml of the individual ozone waters were charged into different measurement cells. Then, the working electrode was disposed such that its tip was in contact with the water surface of the ozone water in a measurement cell. That is, the working electrode was disposed such that the surface area contact with the ozone water was 3.14 mm$^2$ (=1 mm×1 mm×3.14).

Figure 10:
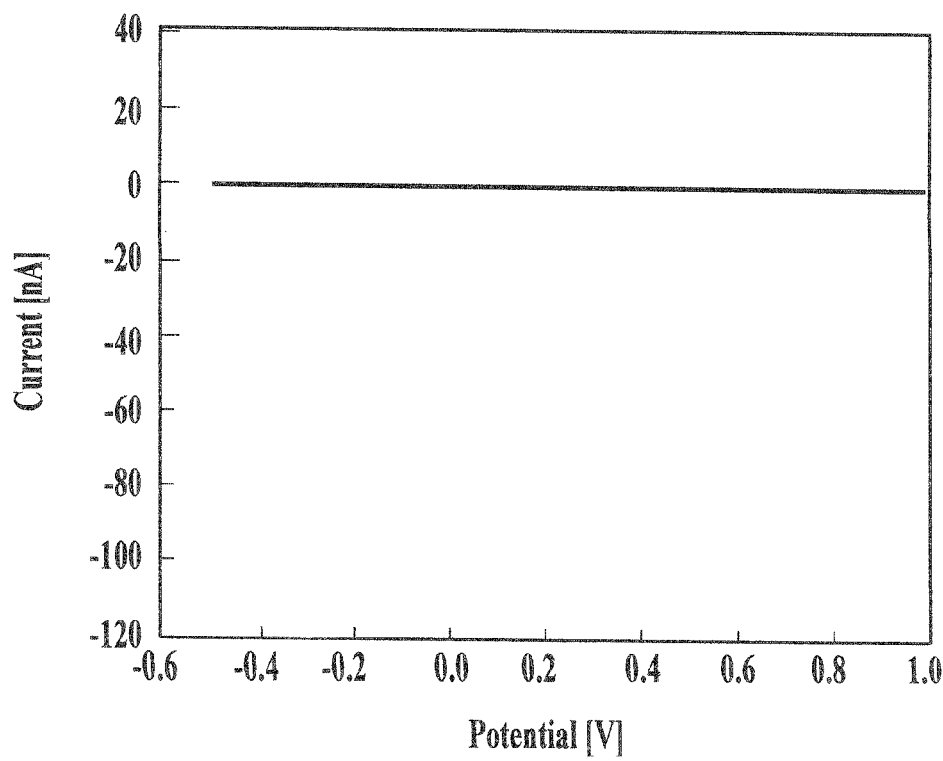
FIG. 10 This is a view of a limiting current-voltage curve (voltammogram) of Comparison 1.

The reference electrode, the counter electrode and the method of measuring limiting current value were the same as Example 1. The obtained limiting current-voltage curve (voltammogram) is shown in FIG. 10.

Thereafter, the limiting current of the ozone waters in the other measurement cells was measured in the same manner. The obtained limiting current-voltage curves are also shown in FIG. 10.

As illustrated in FIG. 11 and FIG. 12, the calibration curves with good correlation between ozone concentration and electric current value were successfully determined in Example 1 and Example 2. Therefore, it can be said that ozone concentration can be measured precisely by using the calibration curves.

As illustrated in FIG. 13, in Example 3, while the calibration curve was successfully determined and ozone concentration can be measured by using the calibration curve, it was found that the accuracy thereof is lower than Example 1 and Example 2.

On the other hand, as illustrated in FIG. 10, in Comparison 1, a calibration curve could not be determined since electric current could not be measured, and it was therefore impossible to perform the concentration measurement.

From the above-described results, it was found that ozone concentration can be measured with high accuracy even for ozone water that contains no electrolyte and has high solution resistance by bringing a working electrode into contact with the ozone water such that the surface area of contact between the working electrode and the ozone water falls within the range of 628 μm$^2$ to 392500 μm$^2$.

From a comparison between Example 1 and Example 2, it was found that the oxygen-terminated electrode has improved accuracy compared to the hydrogen-terminated electrode. It is presumed that this is because oxygen-termination eliminates the influence of the oxidation of the working electrode by ozone, and thereby improves the stability of the working electrode.

In order to achieve the surface area of contact with the sample solution of less than 628 μm$^2$, an attempt was made to produce a working electrode with a tip with an outer diameter of less than 20 μm, but it failed due to production difficulties.

INDUSTRIAL APPLICABILITY

The present invention is suitably applicable to measuring ozone concentration with high accuracy without using an electrolyte.

DESCRIPTION OF REFERENCE NUMERALS

2 Working electrode
3 Reference electrode
4 Counter electrode
100 Ozone water concentration measurement apparatus
S Sample solution

The invention claimed is:

1. An ozone concentration measurement apparatus that comprises a counter electrode and a working electrode and calculates ozone concentration of ozone water by bringing at least the counter electrode and the working electrode into contact with a sample solution of the ozone water and by applying a voltage between the counter electrode and the working electrode to measure an electric current value at the voltage,
   wherein the working electrode is comprised of an electrically conductive diamond electrode,
   wherein a surface area of contact between the working electrode and the ozone water is within a range of 628 μm$^2$ to 392500 μm$^2$, and
   wherein the ozone concentration measurement apparatus determines a limiting current-voltage curve from the voltage and electric current values, and calculates the ozone concentration from a limiting current value at a predetermined voltage on the limiting current-voltage curve based on a predetermined calibration curve.

2. The ozone water concentration measurement apparatus according to claim 1, wherein the electrically conductive diamond electrode is comprised of a boron-doped electrically conductive diamond electrode.

3. An ozone water concentration measurement method for measuring ozone concentration of ozone water, comprising:
   bringing at least a counter electrode and a working electrode into contact with a sample solution of the ozone water;
   applying a voltage between the counter electrode and the working electrode;
   measuring an electric current value at the voltage;

determining a limiting current-voltage curve from the voltage and electric current values; and calculating the ozone concentration from a limiting current value at a predetermined voltage on the limiting current-voltage curve based on a predetermined calibration curve, wherein the working electrode is comprised of an electrically conductive diamond electrode, and wherein a surface area of contact between the working electrode and the ozone water is within a range of 628 $\mu m^2$ to 392500 $\mu m^2$.

4. The ozone water concentration measurement method according to claim 3, wherein no electrolyte is contained in the sample solution.

5. The ozone water concentration measurement method according to claim 4, wherein the electrically conductive diamond electrode is comprised of a boron-doped electrically conductive diamond electrode.

6. The ozone water concentration measurement method according to claim 3, wherein the electrically conductive diamond electrode is comprised of a boron-doped electrically conductive diamond electrode.

* * * * *